(12) United States Patent
Forstinger et al.

(10) Patent No.: US 8,338,649 B2
(45) Date of Patent: Dec. 25, 2012

(54) METHOD FOR THE PRODUCTION OF AROMATIC CARBONYL COMPOUNDS

(75) Inventors: Klaus Forstinger, Babenhausen (DE); Thomas Sommer, Ubstadt-Weiher (DE); Daniel Decker, Liederbach (DE); Andreas Martin, Berlin (DE); Angela Köckritz, Berlin (DE); Michael Kant, Berlin (DE); Alexander Hofmann, Berlin (DE)

(73) Assignee: Weylchem Frankfurt GmbH, Frankfurt Greiesheim (DE)

( * ) Notice: Subject to any disclaimer, the term of this patent is extended or adjusted under 35 U.S.C. 154(b) by 115 days.

(21) Appl. No.: 12/733,445

(22) PCT Filed: Sep. 2, 2008

(86) PCT No.: PCT/EP2008/007147
§ 371 (c)(1),
(2), (4) Date: Jun. 15, 2010

(87) PCT Pub. No.: WO2009/033586
PCT Pub. Date: Mar. 19, 2009

(65) Prior Publication Data
US 2010/0312017 A1 Dec. 9, 2010

(30) Foreign Application Priority Data
Sep. 7, 2007 (DE) .......... 10 2007 042 544

(51) Int. Cl.
*C07C 45/28* (2006.01)
(52) U.S. Cl. .......... 568/311; 568/435; 568/437
(58) Field of Classification Search .......... 568/311, 568/435, 437
See application file for complete search history.

(56) References Cited

U.S. PATENT DOCUMENTS

| | | | |
|---|---|---|---|
| 4,054,607 | A | 10/1977 | Matsuoka et al. |
| 5,648,551 | A | 7/1997 | Borchert et al. |
| 7,273,954 | B2 | 9/2007 | Antognoli et al. |

FOREIGN PATENT DOCUMENTS

| | | |
|---|---|---|
| EP | 0 723 949 B1 | 7/1996 |
| WO | WO 2004 043891 | 5/2004 |

OTHER PUBLICATIONS

International Search Report issued on May 29, 2009 in application No. PCT/EP2008/007147.
Khenkin et al., "Oxygen Transfer From Sulfoxides: Oxidation of Alkylarenes Catalyzed by a Polyoxomolybdate, $[PMo_{12}O_{40}]$," *Journal of the American Chemical Society*, vol. 124, No. 16, pp. 4198-4199, 2002 (Abstract).
Antognoli, "Über die selective Oxidation von methylierten Aromaten zu aromatischen Aldehyden," *Dissertation, Naturwissenschaften, NR*, 2003, retrieved from the Internet: URL:http://e-collection.ethbib.ethz.ch/view/eth:26806.
Khenkin et al., "Oxygen Transfer From Sulfoxides: Oxidation of Alkylarenes Catalyzed by a Polyoxomolybdate, $[PMo_{12}O_{40}]$," *Journal of the American Chemical Society*, vol. 124, No. 16, pp. 4198-4199, 2002 (Full Article).

*Primary Examiner* — Sikarl Witherspoon
(74) *Attorney, Agent, or Firm* — Foley & Lardner LLP

(57) ABSTRACT

The invention relates to a method for the production of an aromatic carbonyl compound by the oxidation of a methyl group or methylene group bonded to the aromatic group in which the aromatic substance is reacted in the presence of an oxidizing agent and a sulphoxide, a sulphoxide being selected for the oxidation of a specific aromatic substance whose ionization potential, in terms of magnitude, differs from the ionization potential of the aromatic substance to be oxidized by a maximum of ±0.25 eV.

9 Claims, No Drawings

METHOD FOR THE PRODUCTION OF AROMATIC CARBONYL COMPOUNDS

The present invention relates to a method for the production of an aromatic carbonyl compound by the oxidation of a methyl group or methylene group bonded to the aromatic group, the aromatic group being reacted in the presence of an oxidising agent and a sulphoxide.

TECHNOLOGICAL BACKGROUND AND STATE OF THE ART

Aromatic carbonyl compounds (aldehydes, ketones) are important intermediates and/or target products in the intermediate product and fine chemicals industry. Apart from conventional synthesis methods using benzal chlorides, for example, environmentally friendly methods for the direct oxidation of alkyl aromatics with atmospheric oxygen are used on an industrial scale. Liquid phase methods, for example methods for the production of benzaldehyde, as well as gas phase methods, for example methods for the synthesis of methoxybenzaldehyde or para-chlorobenzaldehyde, are known (see U.S. Pat. No. 4,054,607, EP 0 723 949). However, these methods cannot generally be used and in a number of cases are affected negatively by low activities, low selectivities and the formation of by-products. In particular in those cases where further substituents are present on the aromatic ring system, the risk of by-products being formed is high.

From WO 2004/043891, a catalytic oxidation method for the production of aliphatic and aromatic carbonyl compounds from starting products is known which exhibit at least one aliphatic and/or aromatically bonded functional group with the formula —[—CH(R)—X]$_n$ with R=H, alkyl or aryl and X=H. The oxidation is carried out in the presence of an oxidising agent and a sulphoxide or sulphide added in catalytic quantities. In an oxidative environment, the sulphoxides and/or sulphides act as oxygen conveyors. Dialkyl sulphoxides, alkyl aryl sulphoxides and diaryl sulphoxides as well as their mixtures and/or corresponding sulphides are mentioned. No information is provided regarding the conversion, selectivity and space-time yield with respect to combinations of specific alkyl compounds with specific sulphoxides and/or sulphides.

Moreover, it is known from the thesis by F. Antognoli (ETH Zurich, 2003) that the ionisation potential can be used to assess the reactivity of differently substituted aromatics. The ionisation potentials of substituted alkyl-aromatic compounds differ significantly from that of unsubstituted toluene and consequently the type and site of the substitution influence the rate of oxidation and/or the selectivity of the reaction. The ionisation potential of the aromatics is decisive for the formation of radical cations R—H$^+$·, the first activation step in oxidation reactions of this type. Since only a very few simple alkyl aromatics and/or corresponding oxidation products have tabulated ionisation potentials, quantum chemical calculations were carried out for further compounds.

Moreover, ionisation potentials of solvents such as e.g. dimethyl sulphoxide (DMSO) are also indicated in the above-mentioned thesis. Surprisingly enough, it has been found that high levels of selectivity for the desired oxidation products occurred in DMSO in a number of instances. In addition, it was found that methyl aromatics which can be oxidised to the aldehydes in good yields have ionisation potentials which are below that of DMSO. Methyl aromatics with higher oxidation potentials than DMSO, on the other hand, cannot be oxidised or only very poorly.

It is the object of the present invention to further improve the yields and selectivities in the above-described catalytic oxidation of alkyl aromatics to aromatic aldehydes with a view to industrial application.

The invention is based on a method for the production of an aromatic carbonyl compound by the oxidation of a methyl group or methylene group bonded to the aromatic group, the aromatic group being reacted in the presence of an oxidising agent.

The invention is based on the finding that surprisingly, the yield of aldehydes and the selectivity of the oxidation method can be increased, if a sulphoxide is additionally present, wherein the ionisation potentials of the aromatic group to be oxidised and of the sulphoxide are adjusted to each other. If a maximum deviation of the ionisation potentials of ±0.25 eV is maintained, the yield and the selectivity with respect to the aldehydes is considerably increased. In comparison with combinations with greater deviations of the ionisation potentials, increases in selectivity of 50-100% are possible. The closer the ionisation potentials of the sulphoxide and aromatic substance are matched to each other, the higher is the yield and selectivity with regard to the aldehydes, as a rule. Without wishing to be bound by a theory, it is assumed that the formation of radical cations plays an important part during the first activation step of the oxidation reaction.

The invention thus solves the above problem by way of a method for the oxidation of alkyl aromatics with an oxidising agent in the presence of a sulphoxide, a sulphoxide being selected for the oxidation of a specific aromatic substance whose ionisation potential deviates, in terms of magnitude, from the ionisation potential of the aromatic substance to be oxidised by a maximum of ±0.25 eV, preferably by a maximum of ±0.2 eV, in particular by maximum ±0.1. eV.

Preferably, alkyl aromatics are compounds with the formula (I)

where a=1-3 and b=0-4,
A represents a mononuclear or multinuclear aromatic ring system which may also contain hetero atoms and
R1 represents $C_1$-$C_{15}$ alkyl, halogen, halogen alkyl, alkoxy, carboxy, alkoxycarbonyl, cyano, amino, amido, sulfonyl, unsubstituted or substituted phenyl as well as unsubstituted or substituted phenoxy.

Insofar as more than one substituent R1 is present, i.e. b=2, 3 or 4, the substituents R1 can be the same or different, i.e. selected independently of each other.

Preferably, A represents an aromatic group with the formula (II)

with m=0-2 and n=0-2 and x=1-3 and y=1-4, where (x+y) is ≦((6+4m)−n).

Moreover, it is preferred for the sulphoxide to be a compound with the formula (III),

wherein R2 and R3 represent independently of each other substituted or unsubstituted radicals selected from among alkyl, aryl, naphthyl and biphenyl.

Particularly preferred R2 or R3 carry one or several substituents from the group of alkyl, halogen, halogen alkyl, methoxy, carboxy, alkoxy carbonyl, cyano, amino, amido, sulphonyl, phenyl and phenoxy.

Particularly preferred compounds of the formula I are p,p'-dimethylbiphenyl, p,p'-dimethylbiphenyl ether, p-methoxytoluene, 4-methyl-2'-cyanobiphenyl, p-xylene, p-bromotoluene, p-chlorotoluene, terephthalaldehyde and p-cyanotoluene.

Particularly preferred compounds with the formula III are 1,1'-dinaphthyl sulphoxide, di-tert-butyl sulphoxide, phenyl benzyl sulphoxide, naphthyl methyl sulphoxide, diisopropyl sulphoxide, diphenyl sulphoxide, bis(p-chlorophenyl) sulphoxide, phenyl methyl sulphoxide, diethyl sulphoxide, dimethyl sulphoxide, trifluoromethyl phenyl sulphoxide, bis(monofluoromethyl) sulphoxide, trifluoromethyl methyl sulphoxide and bis(trifluoromethyl) sulphoxide.

Peroxy compounds such as peroxydisulfate, oxone, hydrogen peroxide, alkyl peroxides, peracids and molecular oxygen can be used as oxidising agent. Peroxydisulfate is particularly preferred.

Finally, it is preferable to determine the ionisation potentials of the sulphoxides and the aromatics to be oxidised according to the B3LYP (Becke 3-Parameter Lee Yang Parr) method.

Molecular orbital calculations are based on the LCAO (linear combination of atomic orbitals) method. The aim of quantum chemical molecular orbital methods is always the determination of the energy of molecules. These are considered as being the entity consisting of atomic nuclei arranged spatially and the surrounding electrons. The electrons are described in quantum mechanical approximation by wave functions. These wave functions are approximated by basis sets (e.g. 3-21G, 6-31G*), the bigger the basis set the more accurate is the calculation. B3LYP/6-31 G* indicates the method and basis set by means of which the calculation is to be carried out. The B3LYP (Becke 3-Parameter Lee Yang Parr) method is a hybrid density functional theory (DFT) method which provides excellent results for small molecules.

In Tables 1 and 2 below, the ionisation potentials for the preferred aromatics and sulphoxides are summarised which have been determined according to the B3LYP method using the basis set 6-31 G*. It deserves to be mentioned that the values deposited in the NIST data bank for ionisation potentials have not been determined according to standardised methods and may therefore be affected by errors. In addition, they are not complete.

TABLE 1

| aromatic substance | Ionisation potential according to B3LYP/6-31G* |
|---|---|
| p,p'-dimethylbiphenyl | 7.5 |
| p,p'-dimethylbiphenyl ether | 7.5 |
| p-methoxytoluene | 7.8 |
| 4-methyl-2'-cyanobiphenyl | 8.1 |
| p-xylene | 8.3 |
| p-bromotoluene | 8.4 |
| p-chlorotoluene | 8.5 |
| terephthalaldehyde | 9.5 |
| p-cyanotoluene | 9.7 |

TABLE 2

| sulphoxide (SO) | Ionisation potential according to B3LYP/6-31G* |
|---|---|
| 1,1'-dinaphthyl SO | 7.5 |
| di-tert-butyl SO | 7.9 |
| phenyl benzyl SO | 7.9 |
| naphthyl methyl SO | 7.9 |
| diisopropyl SO | 8.2 |
| diphenyl SO | 8.2 |
| bis(p-chlorophenyl) SO | 8.3 |
| phenyl methyl SO | 8.4 |
| diethyl SO | 8.5 |
| dimethyl SO | 8.8 |
| trifluoromethyl phenyl SO | 9.1 |
| bis(monofluoromethyl) SO | 9.5 |
| trifluoromethyl methyl SO | 9.8 |
| bis(trifluoromethyl) SO | 10.6 |

Using these data calculated by means of the B3LYP method, pairs consisting of aromatic substance and sulphoxide can be formed in which the ionisation potential differs by maximum ±0.25 eV, preferably by ±0.2 eV, in particular by ±0.1. eV. Table 3 provides a few combinations preferred according to the invention.

TABLE 3

| aromatic substance | sulphoxide(s) |
|---|---|
| p,p'-dimethylbiphenyl | 1,1'-dinaphthyl SO |
| p,p'-dimethylbiphenyl ether | 1,1'-dinaphthyl SO |
| p-methoxytoluene | di-tert. butyl SO, phenyl benzyl SO and naphthyl methyl SO |
| 4-methyl-2'-cyanobiphenyl | diisopropyl SO, diphenyl SO and bis(p-chlorophenyl) SO |
| p-xylene | diisopropyl SO, diphenyl SO, bis(p-chlorophenyl) SO, phenyl methyl SO and diethyl SO |
| p-bromotoluene | diisopropyl SO, diphenyl SO, bis(p-chlorophenyl) SO, phenyl methyl SO and diethyl SO |
| p-chlorotoluene | bis(p-chlorophenyl) SO, phenyl methyl SO and diethyl SO |
| terephthalaldehyde | bis(monofluoromethyl) SO |
| p-cyanotoluene | trifluoromethyl methyl SO |

Surprisingly, it has been found that the oxidation method can be carried out with high yields and a good selectivity if use is made of the pairs of aromatic starting product and sulphoxide indicated in Table 3.

In other respects, the reaction is carried out in the manner known to the expert. The temperature, solvent etc are adjusted to the aromatic substance to be oxidised. In general, the reaction is carried out at temperatures of 40-100° C., with molecular ratios of aromatic substance:sulphoxide of 25:1 to 1:1, preferably 10:1 to 1.1:1, in particular 5:1 to 1.2:1, ratio of aromatic substance:oxidising agent of 1:50 to 1:1 and within a period of 1 to 10 hours. Highly polar solvents such as water, acetonitrile, nitromethane, acetic acid, DMF and other mixtures are used, water and acetonitrile being preferably used.

The following examples are to illustrate the invention in further detail without limiting it, however, to the specific examples described.

EXAMPLE 1

Production of p-Chlorobenzaldehyde from p-Chlorotoluene a) p-Chlorotoluene/Dimethyl Sulphoxide System (Not According to the Invention)

5.06 g (40 mmole) of 4-chorotoluene, 90 ml of acetonitrile and 2 ml (28.2 mmole) of dimethyl sulphoxide (DMSO) are introduced with stirring into a 500 ml 3-necked flask flushed with argon and preheated to the reaction temperature (70° C.).

187.3 mg (0.75 mmole) of $CuSO_4 \times 5H_2O$ and 81.8 mg (0.30 mmole) of $FeSO_4 \times 7H_2O$, dissolved in 15 ml of water, are added. The solution is stirred vigorously for 10 min. Subsequently, a solution of 22 g of $Na_2S_2O_8$ (92.4 mmole) in 60 ml of water is added with further vigorous stirring within 60 min using a syringe pump. The reaction solution is stirred for a further 3 h at 70° C.

Following the end of the reaction and cooling to room temperature, ethyl acetate is added, the two-phase mixture is separated and the aqueous phase is extracted exhaustively with further ethyl acetate.

The combined organic phases are collected and dried over $Na_2SO_4$. The composition of the product is determined by GC or HPLC.

The yield of p-chlorobenzaldehyde is 38%. The difference between the ionisation potentials is 0.3 eV.

b) p-Chlorotoluene/(Methylphenyl) Sulphoxide System (According to the Invention)

5.06 g (40 mmole) of 4-chorotoluene, 90 ml of acetonitrile and 3.96 g (28.2 mmole) of (methylphenyl) sulphoxide are introduced with stirring into a 500 ml 3-necked flask flushed with argon and preheated to the reaction temperature (70° C.). 187.3 mg (0.75 mmole) of $CuSO_4 \times 5H_2O$ and 81.8 mg (0.30 mmole) of $FeSO_4 \times 7H_2O$, dissolved in 15 ml of water, are added. The solution is stirred vigorously for 10 min. Subsequently, a solution of 22 g of $Na_2S_2O_8$ (92.4 mmole) in 60 ml of water is added with further vigorous stirring within 60 min using a syringe pump. The reaction solution is stirred for a further 3 h at 70° C.

Following the end of the reaction and cooling to room temperature, ethyl acetate is added, the two-phase mixture is separated and the aqueous phase is extracted exhaustively with further ethyl acetate.

The yield of p-chlorobenzaldehyde is 58%. Compared with the reaction with DMSO as sulphoxide, the yield is thus higher by a factor of 1.53. The difference between the ionisation potentials is only 0.1 eV in this case.

c) p-Chlorotoluene/Bis(p-Chlorophenyl) Sulphoxide System (According to the 5.06 g (40 mmole) of p-chorotoluene, 90 ml of acetonitrile and 7.64 g (28.2 mmole) of bis(p-chlorophenyl) sulphoxide are introduced with stirring into a 500 ml 3-necked flask flushed with argon and preheated to the reaction temperature (70° C.). 187.3 mg (0.75 mmole) of $CuSO_4 \times 5H_2O$ and 81.8 mg (0.30 mmole) of $FeSO_4 \times 7H_2O$, dissolved in 15 ml of water, are added. The solution is stirred vigorously for 10 min. Subsequently, a solution of 22 g of $Na_2S_2O_8$ (92.4 mmole) in 60 ml of water is added with further vigorous stirring within 60 min using a syringe pump. The reaction solution is stirred for a further 3 h at 70° C.

Following the end of the reaction and cooling to room temperature, ethyl acetate is added, the two-phase mixture is separated and the aqueous phase is extracted exhaustively with further ethyl acetate.

The yield of p-chlorobenzaldehyde is 50%. Compared with the reaction with DMSO as sulphoxide, the yield is thus higher by a factor of 1.32. The difference between the ionisation potentials is 0.2 eV in this case.

d) p-Chlorotoluene/Trifluoromethyl Phenyl) Sulphoxide System (Comparison)

5.06 g (40 mmole) of 4-chorotoluene, 90 ml of acetonitrile and 5.48 g (28.2 mmole) of (trifluoromethyl phenyl) sulphoxide are introduced with stirring into a 500 ml 3-necked flask flushed with argon and preheated to the reaction temperature (70° C.). 164.8 mg (0.66 mmole) of $CuSO_4 \times 5H_2O$ and 60 mg of $FeSO_4 \times 7H_2O$ (0.22 mmole), dissolved in 15 ml of water, are added. The solution is stirred vigorously for 10 min. Subsequently, a solution of 22 g of $Na_2S_2O_8$ (92.4 mmole) in 60 ml of water is added with further vigorous stirring within 60 min using a syringe pump. The reaction solution is stirred for a further 3 h at 70° C.

Following the end of the reaction and cooling to room temperature, ethyl acetate is added, the two-phase mixture is separated and the aqueous phase is extracted exhaustively with further ethyl acetate.

The yield of p-chlorobenzaldehyde is 14%. Compared with the reaction with DMSO as sulphoxide, the yield amounts to only a factor of 0.37. The difference between the ionisation potentials is 0.6 eV in this case.

EXAMPLE 2

Production of p-Bromobenzaldehyde from p-Bromotoluene a) p-Bromotoluene/Dimethyl Sulphoxide (Not According to the Invention)

6.84 g (40 mmole) of 4-bromotoluene, 80 ml of acetonitrile and 1.8 ml (25.4 mmole) of dimethy sulphoxide (DMSO) are introduced with stirring into a 500 ml 3-necked flask flushed with argon and preheated to the reaction temperature (70° C.). 149.8 mg (0.60 mmole) of $CuSO_4 \times 5H_2O$ and 95.5 mg (0.35 mmole) of $FeSO_4 \times 7H_2O$, dissolved in 15 ml of water, are added. The solution is stirred vigorously for 10 min. Subsequently, a solution of 21 g of $Na_2S_2O_8$ (88.2 mmole) in 70 ml of water is added with further vigorous stirring within 60 min using a syringe pump. The reaction solution is stirred for a further 1 h at 70° C.

Following the end of the reaction and cooling to room temperature, methylene chloride is added, the two-phase mixture is separated and the aqueous phase is extracted exhaustively with further methylene chloride.

The yield of p-bromobenzaldehyde is 34%. The difference between the ionisation potentials is 0.4 eV.

b) p-Bromotoluene/Diphenyl Sulphoxide (According to the Invention)

6.84 g (40 mmole) of 4-bromotoluene, 80 ml of acetonitrile and 5.14 g (25.4 mmole) of diphenyl sulphoxide (IP=8.2/8.6) are introduced with stirring into a 500 ml 3-necked flask flushed with argon and preheated to the reaction temperature (70° C.). 149.8 mg (0.60 mmole) of $CuSO_4 \times 5H_2O$ and 95.5 mg (0.35 mmole) of $FeSO_4 \times 7H_2O$, dissolved in 15 ml of water, are added. The solution is stirred vigorously for 10 min. Subsequently, a solution of 21 g of $Na_2S_2O_8$ (88.2 mmole) in 70 ml of water is added with further vigorous stirring within 60 min using a syringe pump. The reaction solution is stirred for a further 1 h at 70° C.

Following the end of the reaction and cooling to room temperature, methylene chloride is added, the two-phase mixture is separated and the aqueous phase is extracted exhaustively with further methylene chloride.

The yield of p-bromobenzaldehyde is 66%. Compared with the reaction with DMSO as sulphoxide, the yield is thus higher by a factor of 1.94. The difference between the ionisation potentials is 0.2 eV in this case.

c) p-Bromotoluene/Di(Tert-Butyl) Sulphoxide (Comparison)

6.84 g (40 mmole) of 4-bromotoluene, 80 ml of acetonitrile and 4.12 g (25.4 mmole) of di(tert-butyl) sulphoxide (IP=7.9/8.2) are introduced with stirring into a 500 ml 3-necked flask flushed with argon and preheated to the reaction temperature (70° C.). 149.8 mg (0.60 mmole) of $CuSO_4 \times 5H_2O$ and 95.5 mg (0.35 mmole) of $FeSO_4 \times 7H_2O$, dissolved in 15 ml of water, are added. The solution is stirred vigorously for 10 min. Subsequently, a solution of 21 g of $Na_2S_2O_8$ (88.2 mmole) in 70 ml of water is added with further vigorous stirring within 60 min using a syringe pump. The reaction solution is stirred for a further 1 h at 70° C.

Following the end of the reaction and cooling to room temperature, methylene chloride is added, the two-phase mixture is separated and the aqueous phase is extracted exhaustively with further methylene chloride.

The yield of p-bromobenzaldehyde is 15%. Compared with the reaction with DMSO as sulphoxide, the yield amounts to only a factor of 0.44. The difference between the ionisation potentials is 0.5 eV in this case.

The invention claimed is:

1. Method for the production of an aromatic carbonyl compound, comprising oxidizing a methyl group or methylene group bonded to the aromatic group of an aromatic substance in the presence of an oxidising agent and a sulphoxide,
    wherein the ionisation potentials, calculated according to the Becke 3-Parameter Lee Yang Parr method, of the aromatic substance and the sulphoxide do not differ from each other by more than ±0.25 eV, and
    wherein the ratio of aromatic substance to sulfoxide is from 25:1 to 1.1:1.

2. Method according to claim 1 in which the aromatic substance is a compound of formula (I)

(I)

where
a=1-3 and b=0-4;
A represents a mononuclear or multinuclear aromatic ring system which may also contain hetero atoms and
R1 represents $C_1$-$C_{15}$ alkyl, halogen, halogen alkyl, alkoxy, carboxy, alkoxy carbonyl, cyano, amino, amido, sulfonyl, unsubstituted or substituted phenyl and unsubstituted or substituted phenoxy.

3. Method according to claim 2 in which A represents an aromatic group of formula (II)

(II)

with m=0-2 and n=0-2 and x=1-3 and y=1-4,
where (x+y) is $\leq((6+4m)-n)$.

4. Method according to claim 1 in which the sulphoxide is a compound of formula (III)

(III)

where R2 and R3 represent independently of each other substituted or unsubstituted radicals selected from the group comprising alkyl, aryl, naphthyl and biphenyl.

5. Method according to claim 4 in which R2 or R3 carry one or several substituents from the group of alkyl, halogen, halogen alkyl, methoxy, carboxy, alkoxy carbonyl, cyano, amino, amido, sulphonyl, phenyl and phenoxy.

6. Method according to claim 1 in which a sulphoxide is selected whose ionisation potential, in terms of magnitude, differs from the ionisation potential of the aromatic substance to be oxidised by not more than ±0.2 eV.

7. Method according to claim 6 wherein the ionisation potential of the sulphoxide differs from the ionisation potential of the aromatic substance by not more than ±0.1 eV.

8. Method according to claim 1, wherein the ratio of aromatic substance to sulfoxide is from 10:1 to 1.2:1.

9. Method according to claim 8 wherein the ratio of aromatic substance to oxidizing agent is 1:50 to 1:1.

* * * * *